United States Patent [19]

Nishikawa

[11] Patent Number: 4,661,967
[45] Date of Patent: Apr. 28, 1987

[54] DENTAL RADIOGRAPHIC APPARATUS FOR PHOTOGRAPHING ENTIRE JAWS

[75] Inventor: Kazuo Nishikawa, Kyoto, Japan

[73] Assignee: Kabushiki Kaisha Morita Seisakusho, Kyoto, Japan

[21] Appl. No.: 667,769

[22] Filed: Nov. 2, 1984

[30] Foreign Application Priority Data

Nov. 12, 1983 [JP] Japan .................. 58-212992

[51] Int. Cl.⁴ .................. A61B 6/14; G03B 41/16
[52] U.S. Cl. .................. 378/39; 378/40
[58] Field of Search .................. 378/38, 39, 40

[56] References Cited

U.S. PATENT DOCUMENTS

| | | | |
|---|---|---|---|
| 3,737,660 | 6/1973 | Ando et al. .................. | 378/39 |
| 4,039,837 | 8/1977 | Ohta et al. .................. | 378/40 |
| 4,263,513 | 4/1981 | Palluet .................. | 378/40 |

Primary Examiner—Craig E. Church
Assistant Examiner—T. N. Grigsby
Attorney, Agent, or Firm—Koda and Androlia

[57] ABSTRACT

A dental radiographic apparatus for photographing the entire jaws in which the apparatus includes a rotary arm having an X-ray source at one end and an X-ray film cassette at the other end thereof and operating in the manner that a path of movement of X-ray beam with respect to the dental arch describer a symmetrically extending approximately triangular envelope projecting toward the front tooth region of the dental arch by sequentially shifting the center of rotation of the X-ray beam irradiated from the X-ray source upon the X-ray film cassette, the apparatus being characterized in that it comprises a means for changing the straight-line distance on the medial line of the human body between the apex and receding points of limit of the envelope.

1 Claim, 10 Drawing Figures

DENTAL RADIOGRAPHIC APPARATUS FOR PHOTOGRAPHING ENTIRE JAWS

FIELD OF THE INVENTION

1. Background of the Invention

This invention relates to improvements in dental radiographic apparatus for photographing the entire jaws.

2. Prior Art

In view of the fact that the dental arch of the human body is approximately arcuate, a dental radiographic apparatus for examination of the entire jaws is designed to move an X-ray source and an X-ray film cassette in opposed relation with respect to each other so that their paths of movement may be approximately arcuate and to take a radiograph of the jaws in their course of movement, and is usually provided with an X-ray source at one end and an X-ray film cassette at the other end of a rotary arm so as to impart combined driving force of linear movement and rotary movement to the rotary arm. Under this driving mechanism are known to be included a biaxial control system, a planetary gear system, guiding plate system, three centers of rotation (also called orthopantomography) system, and the like, but movement of X-ray beam irradiated from an X-ray source upon an X-ray film cassette describes a path of envelope indicated by $A_1$ in FIG. 1, when the arm makes approximately elliptically arcuate movement under any one of the systems. Namely, the X-ray beam is required to rotate so as to make incidence at substantially right angles with the elliptically arcuate dental path. For example, suppose that the instantaneous center of rotation of X-ray beams $B_{11}$, $B_{12}$ and $B_{13}$ irradiated upon the dental arch on the left side of the drawing are $A'_{11}$, $A'_{12}$, and $A'_{13}$, respectively, the X-ray beams in the center of the front tooth region E is on the medial line 0—0, and the center of rotation of the X-ray beam becomes $a_1$ and continuously moves likewise with respect to the dental arch on the right side, so that the path of movement forms an envelope $A_1$. The path of this envelope describes an approximately triangular (or inverted V-shaped) curve which, with an apex $a_1$ as a boundary, moves back symmetrically toward both sides of the dental arch and leads curvedly to the right and left receding points of limit $b_1$ and $b_1$, the apex $a_1$ projecting toward the front tooth region E of the dental arch $C_1$ on the medial line 0—0 of the human body, and the path corresponds to the configuration of a so-called "envelope" of the X-ray beam irradiated upon the dental arch. Accordingly, the path of the envelope described above is defined hereinafter as an envelope of the X-ray beam irradiated upon the dental arch in order to make it easy to understand the invention. Thus, this envelope may also be a path of instantaneous center of rotation of X-ray beam.

By the way, the conventional biaxial control system or other systems are simply operated in the manner that the configuration of the envelope of the X-ray beam irradiated upon the dental arch is definite and the definite configuration of envelope $A_1$ is shifted back and forth in accordance with the front tooth position of a patient and a tomographic position is also shifted back and forth in accordance with the front tooth position of a patient, and problems of improving the right-angled incidence of X-ray beam upon the dental arch and further exluding ghost images of the mandibular ramuses is left unsolved.

A more concrete description will be given of the disadvantages inherent in the conventional systems with reference to FIG. 1. The radiographic apparatus is definite in the configuration of inherent X-ray beam irradiated on the dental arch. The position of the dental arch C of a patient with respect to the radiographic apparatus is first designated as C hd 1 ($C_1$ is designated as the dental arch for simplicity's sake in the description that follows, and the same is the case with $C_2$.), and the radiographic apparatus is moved in the manner that the tomographic position may be moved to $C_1$ in accordance with this position of the dental arch and X-ray beam $B_{11}$ may move along an envelope $A_1(b_1$- $a_1$- $b_1)$. If the position of the dental arch C of a patient is shifted to a position $C_2$, X-ray beam $B_2$ is shifted to another envelope $A_2(b_2$- $a_2$- $b_2)$ in the manner that the tomographic position may be moved to $C_2$ in accordance with the position $C_2$.

Since in this shifted position the envelopes $A_1(b_1$-$a_1$-$b_1)$ and $A_2(b_2$- $a_2$ -$b_2)$ are entirely the same in configuration, the respective angles of incidence of X-ray beams $B_1$ and $B_2$ corresponding to the dental arches $C_1$ and $C_2$ do not change and, since the respective X-ray beams transmit through the right and left mandibular ramuses $D_1$, $D_1$ and $D_2$, $D_2$ of a patient in either case of the dental arches $C_1$ and $C_2$, there are produced ghost images which are pictured white on the X-ray film.

The characters $A'_{11}$ and $A'_2$ designate a position of instantaneous center of rotation of the X-ray beam $B_{11}$ irradiated on the dental arch $C_1$ and a position of instantaneous center of rotation of the X-ray beam irradiated on the dental arch $C_2$, respectively. Namely, in order to obtain an optimum picture for dental examination, it is conventionally necessary that the X-ray beam $B_{11}$ be irradiated on the dental arch $C_1$ at approximately right angles with the arch $C_1$. When, for example, an envelope $A_1$ intended for an adult male is selected so as to fulfill this requirement, the requirement is not fulfilled in the case of a female and a child whose dental arches are smaller than $C_1$, with the result that there is produced a ghost image of the teeth.

On the other hand, the mandibular ramuses $D_1$ and $D_2$ have grown better in the case of adults than in the case of children as shown in FIG. 1. Accordingly, when the molar tooth region is photographed in the state of right-angled irradiation of X rays, the center of rotation of X-ray beam $B_{11}$ on the envelope $A_1$ is, for example on point $A'_{11}$, with the result that the X-ray beam $B_{11}$ is irradiated upon the molar tooth after having transmitted through the manidubular ramus $D_1$, which fact, because of the ghost image of the mandibular ramus, makes it difficult for a dentist to diagnose an affected part or makes him liable to overlook the part when he examines the X-ray film.

SUMMARY OF THE INVENTION

Accordingly, an object of the invention is to provide an apparatus which makes it possible to select a state of photographing (a configuration of envelope) in which, irrespective of whether a patient is an adult male, female or child, X rays can always be irradiated upon the dental arch at substantially right angles with the arch, and simultaneously a state of photographing in which the ghost images of the manidibular ramuses can be excluded.

The invention is characterized in that the center of rotation of X-ray beam is not caused to describe a single fixed path of envelope but is caused to change configuration and path of the envelope stepwise or steplessly in accordance with the mass of the dental arch to be photographed, the mass of the mandibular ramuses or the object of photographing.

DETAILED DESCRIPTION OF THE INVENTION

Figure 1:
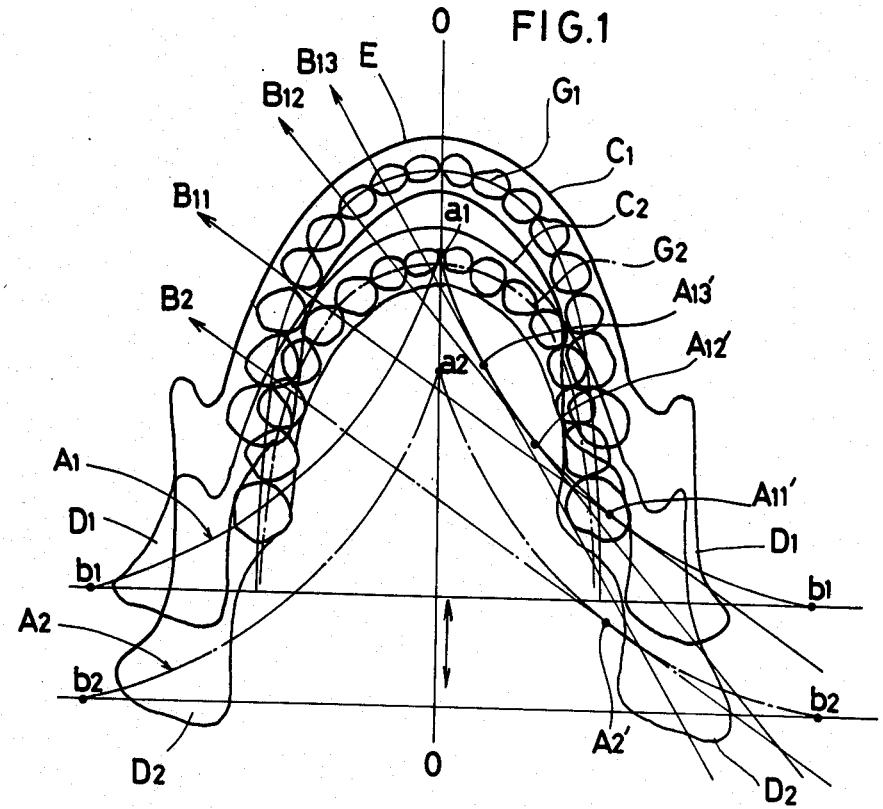
FIG. 1 is a diagrammatic view explaining the principle of a conventional apparatus and showing the relation between the dental arch and the envelope.
Figure 2:
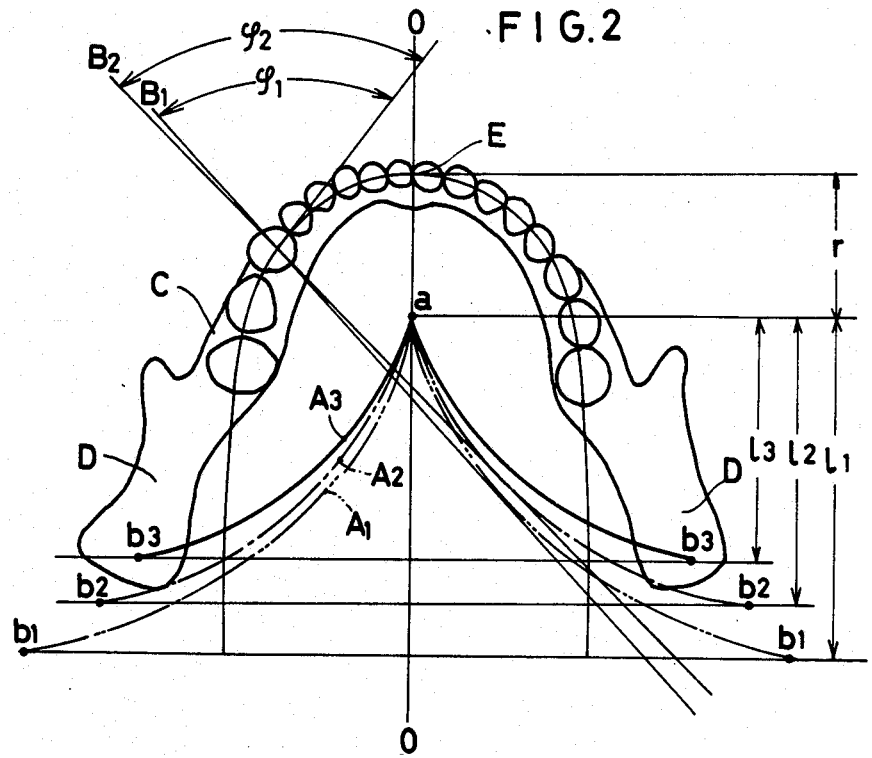
FIGS. 2 and 3 are diagrammatic views explaining the principle of the invention.
Figure 3:
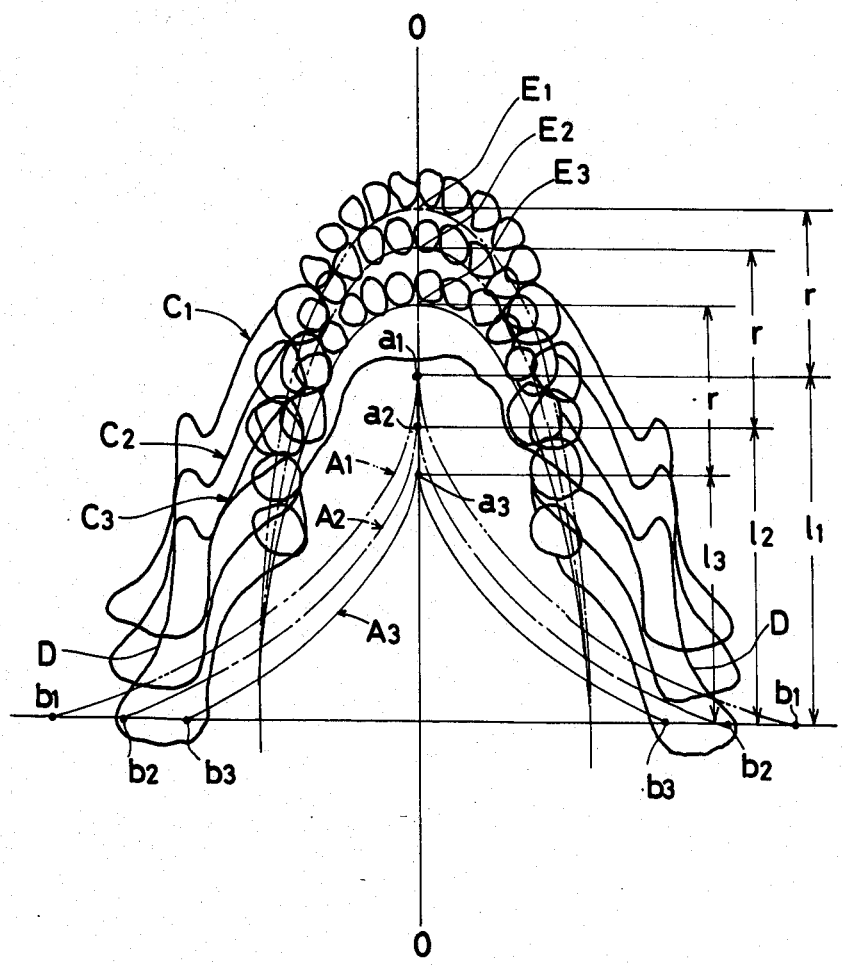

As shown in FIG. 1, an envelope $A_1$ recedes symmetrically and curvedly toward both sides of the molar tooth region with an apex $a_1$ as a boundary, the apex projecting toward the front tooth region E of the dental arch C on the medial point 0—0 of the human body, and thus the envelope $A_1$ described an approximately triangular (or inverted V-shaped) path of curve extending between the apex $a_1$ and the right and left receding points of limit $b_1$ and $b_1$. According to the principle of the invention, there are provided two types of structure, one being of the type in which, as shown in FIG. 2, the apex a of envelope is fixed longitudinally in response to a change in the dental arch C and in which the straight-line distance $l_1$ between the apex a and the right and left receding points of limit $b_1$ and $b_1$ is caused to change into straight-line distance $l_2$ and $l_3$ and the other being of the type in which, as shown in FIG. 3, the receding point of limit b of envelope is longitudinally fixed and the straight-line distance $l_1$ is caused to change into $l_2$ and $l_3$. The difference between the two types is as follows. According to the type of FIG. 2, the apex a of the envelope is fixed and the distance r from the apex a to the front tooth region E is definite, and accordingly even if the envelope of X-ray beam with respect to the dental arch changes, the tomographic position of the front tooth region does not change, so that there is no necessity of the dental arch C(namely the head of the human body) being moved. In the type of FIG. 3, the apex a is moved along the medial point 0—0 and the position of receding points of limit is longitudinally fixed to enable a change in the envelope with the distance r from the apex a of the envelope to the front tooth region E kept definite in response to a change in the dental arch C, so that the FIG. 3 type is simplified in point of mechanism, but in response to a change in the envelope it is necessary to move the dental arch (namely the head of the human body) with respect to a radiographic apparatus. But both of the types are the same in that they changes the configuration of the envelope of the X-ray beam.

If, in FIGS. 2 and 3, the envelope is changed from $A_3(b_3$- $a_3$- $b_3)$ to $A_1(b_1$- $a_1$- $b_1)$, the ghost image of the mandibular ramus D can be excluded from X-ray irradiation, as apparent from the drawings, and if the envelope is changed from $A_1$ ($b_1$- $a_1$- $b_1$) to $A_3(b_3$- $a_3$- $b_3)$, it becomes possible to change an angle of incidence of X-ray beam with the dental arch C, especially to achieve right-angled incidence of X-ray beam upon the dental arches of an adult female and a child whose dental arches are smaller than those of an adult male. For example, if the envelope is changed from $A_1(b_1$- $a_1$- $b_1)$ to $A_2(b_2$- $a_2$- $b_2)$, it is possible to change the angle of incidence of X-ray beam in FIG. 2 from $\phi_1$ to $\phi_2$. Incidentally, it may sometimes happen that the right-angled irradiation of X rays upon the teeth is imparted when the ghost image of the mandibular ramus D is evaded. But all that is necessary to do in this respect is to make preferential selection of the right-angled irradiation of X rays or exclusion of the ghost image in the mandibular ramus in consideration of which one is more important, depending upon the region to be photographed.

Figure 4:
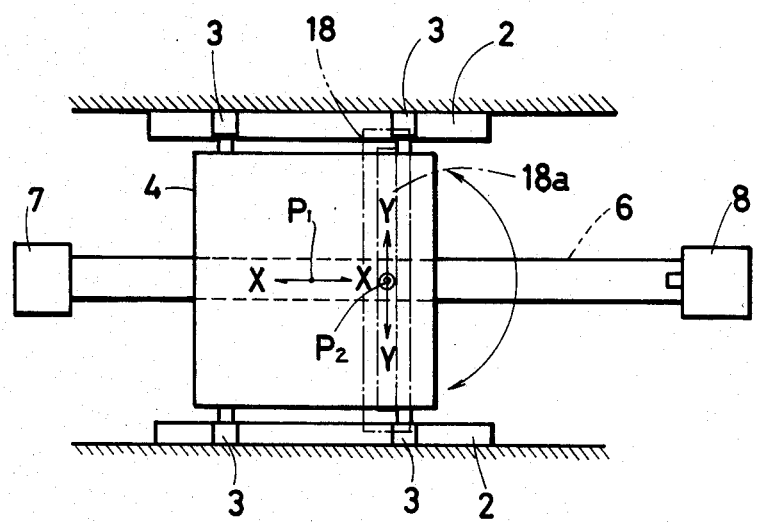
FIG. 4 is a schematic view of one embodiment of the apparatus according to the invention.

A description will now be given of the apparatus of the invention with reference to an embodiment shown in FIG. 4 and those that follow.

FIGS. 4 to 9 show a apparatus corresponding to a drawing explaining the principle of the invention in FIG. 3. Parallelly arranged on both sides of the underside of a fixed frame 1 are rail beds 2 and 2. A slider 4 is slidably mounted in the rail beds 2 and 2 so as to travel along the rail beds in the direction of arrow X—X. It is to be noted that the slider is provided with rollers 3 . . . in rollable engagement with the rail beds 2 and 2. As apparent from FIGS. 5, 7 and 8, the slider is vertically formed in the middle with a through-hole 4b enclosed with a cylinder part 4a, and a horizontal rotary arm 6 is rotatably mounted on the cylinder part 4a through a bearing 5. This horizontal arm 6 is suspendedly provided at one end with an X-ray cassette 7 and at the other end with an X-ray source 8, and the rotating force of the motor mounted on the arm 6 is imparted from a pulley 10 on the output shaft of the motor 9 to a pulley 12 of the slider 4 through a belt 11 to rotate the arm 6. It is to be understood that the center of rotation $P_1$ of the arm 6 at this junction (see FIG. 4) lies on the axis of the cylinder part 4a.

Figure 5:
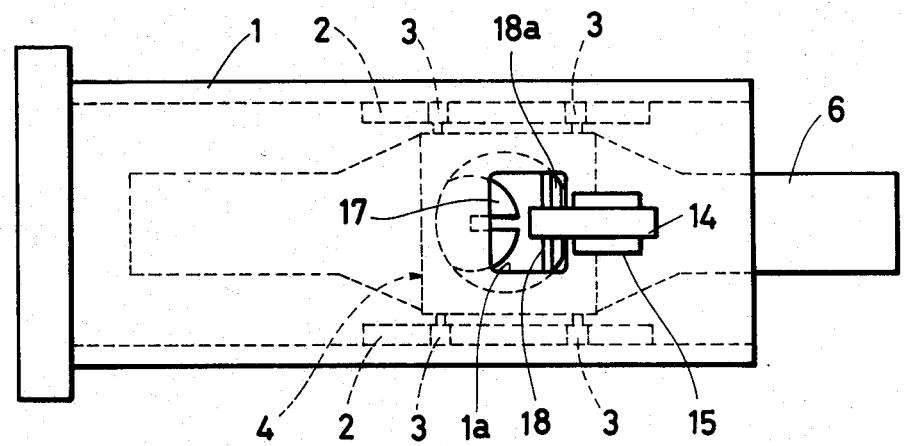
FIG. 5 is a plan view of the embodiment in FIG. 4.
Figure 6:
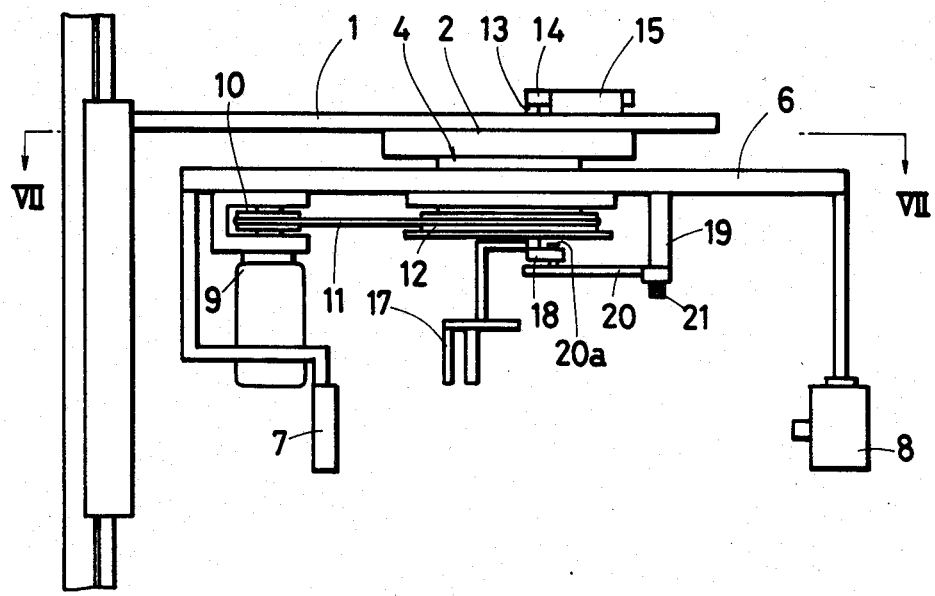
FIG. 6 is a front view of the apparatus in FIG. 4.
Figure 7:
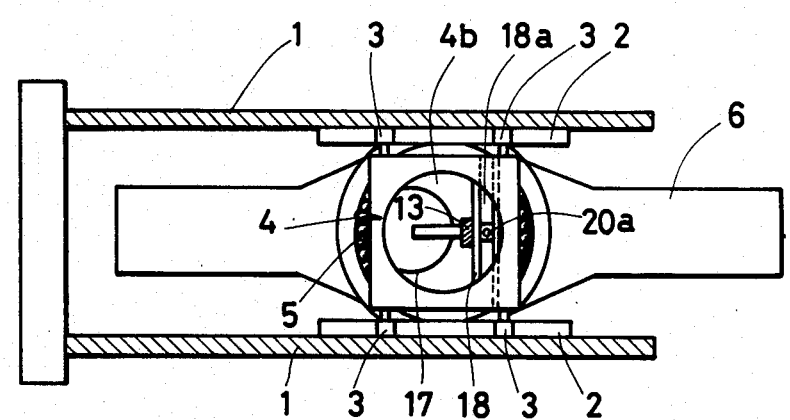
FIG. 7 is a sectional view taken along the line VII—VII seen in the direction of arrow.
Figure 8:
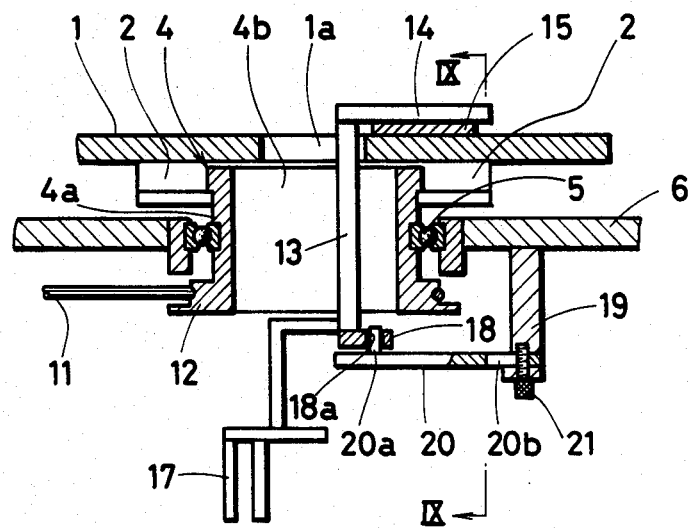
FIG. 8 is a longitudinal sectional view of the essential part of the apparatus of the invention.
Figure 9:
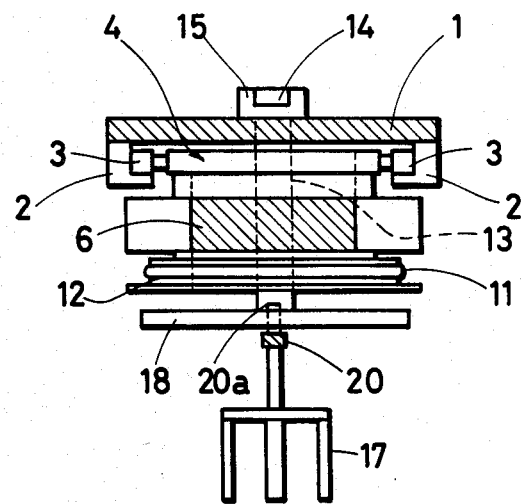
FIG. 9 is a sectional view taken along the line IX—IX seen in the direction of arrow.

The fixed frame 1 is formed right above the slider with a suitable opening 1a as shown in FIGS. 5 and 8. A suspension rod 13 passes through this opening 1a and the aforestated through-hole 4b. To the upper end of this suspension rod 13 is integrally connected to a horizontal rod 14, and the rod 14 is fixed to a stationary bed 15 on the upper surface of the frame. The rod 13 passes through the hole 4b downwardly of the pulley 12 and a head fixer 17 is suspended below the pulley 12. Accordingly, even when the slider 4 slides in the direction of arrow X—X as will later be described, the head fixer 17 keeps its definite position. Also, at the lower end of the suspension rod 13 is suspended a controller 18 having a control groove 18a along in the transverse direction of arrow Y—Y intersecting at right angles with the direction X—X in which the slider 4 slides, and a support rod 20 is extended from a suspension rod 19 suspended from the arm 6 to the controller 18, and an upright guide pin 20a set in the suspension rod 20 is fitted into the control groove 18a. The center position of this groove 18a or of the pin 20a, namely a point $P_2$(see FIG. 4) is eccentric in the direction of arrow X—X with respect to the point $P_1$ and this amount of eccentricity corresponds to the straight-line distance l described in FIGS. 2 and 3. To change the distance l, the support rod 20 is designed to adjust the distance between the controller 18 and the suspension rod 19, and in this adjusted position the rod 20 is fixed to the suspension rod 19 by a lock bolt 21 passing through a long hole 20b of the rod 20. This adjusting means may be dependent upon the long hole stated above or upon other means.

In the construction above, when the motor 9 is actuated for X-ray photographing, the arm 6 starts moving around the axis of rotation $P_1$, namely, the cylindrical portion 4a of the slider 4. At the same time, because a guide pin 20a fits into the control groove 18a in a position eccentric at point $P_2$ with respect to the center of rotation $P_1$, force of movement in the direction of arrow Y—Y is imparted to the arm 6 in accordance with the movement of the arm 6 around the cylinder part of the slider 4, with the result that the slider 4 and the arm 6 are moved in the direction of arrow X—X through rollers 3 . . . in rotable engagement with the rail beds 2 and 2. Through this movement, the arm 6 makes a combined movement in the form of rotational motion and movement in the direction of arrow X—X, and the center of rotation of X-ray beam describes an envelope A, and the X-ray source 8 and the X-ray film cassette 7 make an approximately elliptical arcuate movement along the dental arch.

In the radiographic apparatus of the type described above, releasing a support rod 20 from a suspension rod 19 by loosening a lock bolt 21 in accordance with a patient to be treated makes it possible for the slider 4, rotary arm 6, suspension rod 19 to move in unison in the direction of arrow X—X with respect to the fixed frame 1, suspension rod 19, guide pin 20a, support rod 20, so that the axis of rotation $P_1$ of slider is shifted and the amount of eccentricity of point $P_2$, namely, the straight-line distance l can freely be changed.

Accordingly, it is possible to obtain an optimum X-ray picture for dental examination by selection of the configuration of the envelope in accordance with the size of the dental arch of a patient and an object of radiographing before starting radiographing. In this apparatus it is possible to change the envelope wich fixes the receding points of limit of an envelope in the embodiment in FIG. 3.

Figure 10:
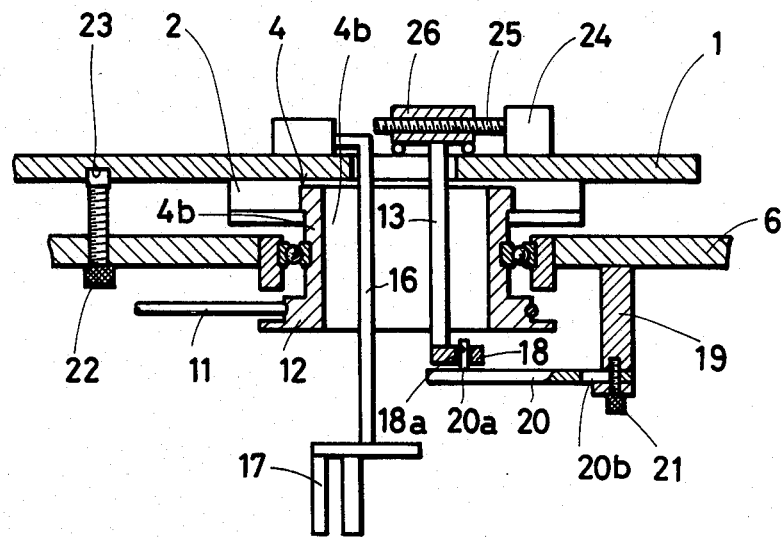
FIG. 10 is a longitudinal sectional view of the essential part of a modified embodiment of the apparatus of the invention.

To effect the change of an envelope in FIG. 2 embodiment by changing the l, the head fixer 17 is detached from the suspension rod 13 as shown in FIG. 10 and is fixed to the fixed frame 1. And after the lock bolt 22 threaded into the arm 6 is inserted into the lock hole 23 of the frame 1 and fixed thereto so that the horizontal rotary arm 6 may not rotate unexpectedly when the distance l is changed, a lock bolt 21 is loosened and the position of the suspension rod 13 is shifted by moving a shifter 26 by a ball screw 25 rotated by motor 24 fixed to the frame 1, the controller 18, guide pin 20a, and support rod 20 are shifted in unison with respect to the fixed frame 1 and horizontal rotary arm 6. By this shift, the lock bolt 21 is tightened in the state in which the predetermined envelope is selected, and then the lock bolt 22 is drawn from the lock hole 23 to allow the apparatus to be used.

In the structure described above, the control groove 18a of the controller 18 extends in a straight line in the direction of arrow Y—Y, but it is not objectionable to extend the groove 18a arcuately as seen in Japanese Utility Model Application Ser. No. 199698/1983.

In the description of the drawings above, a description is given of the structure of the center of rotation $P_1$ of the horizontal rotary arm moving on the medial line of a patient, but the structure of the apparatus is not limited to the one described but may be applied to the structure in which the path of center of rotation of the arm is vertical to the medial or to the structure in which the center of rotation of the arm describes other paths of movement. The principle of the invention may equally apply to the modified structure above.

Although the structure of the embodiment shown is dependent upon a biaxial control system for its driving system, it is to be understood that it permits the application of the invention also to other systems such as a planetary gear system, guiding plate system, and three centers of rotation system.

Having described my invention as related to the embodiment shown in the accompanying drawings, it is my intention that the invention be not limited by any of the details of description unless otherwise specified, but rather be construed broadly within its spirit and scope as set out in the accompanying claims.

What is claimed is:

1. A dental radiographic apparatus for photographing the entire jaws in which the apparatus includes a rotary arm having an X-ray source at one end and an X-ray film cassette at the other end thereof and having means for moving an X-ray beam of the X-ray source with respect to the dental arch so that said beam describes a symmetrically extending approximately triangular envelope projecting toward the front tooth region of the dental arch by sequentially shifting the center of rotation of the X-ray beam irradiated from the X-ray source upon the X-ray film cassette, said apparatus being characterized in that it comprises a means for changing the straight-line distance on the medial line of the human body between the apex and the line joining the receding points of limit of the envelope, said means for changing the straight-line distance on the medial line between the apex and the line joining the receding points of limit of the envelope changes the straight-line distance on the medial line of the human body between the apex and the line joining the receding points of limit of the envelope by varying the position of the receding points of limit without changing the position of the apex of the envelope.

* * * * *